(12) United States Patent
Senzig et al.

(10) Patent No.: US 7,016,457 B1
(45) Date of Patent: Mar. 21, 2006

(54) MULTIMODE IMAGING SYSTEM FOR GENERATING HIGH QUALITY IMAGES

(75) Inventors: Robert F. Senzig, Germantown, WI (US); Hui David He, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/451,965

(22) Filed: Nov. 30, 1999

Related U.S. Application Data

(60) Provisional application No. 60/114,479, filed on Dec. 31, 1998.

(51) Int. Cl.
*G01N 23/00* (2006.01)
(52) U.S. Cl. ......................... 378/19; 378/116
(58) Field of Classification Search ............... 378/98.8, 378/116, 193, 195, 197, 189, 21–27, 4, 41–42, 378/156–157, 122, 205, 8, 20, 62, 98.12, 378/14, 19
See application file for complete search history.

(56) References Cited

U.S. PATENT DOCUMENTS

| | | | | | |
|---|---|---|---|---|---|
| 4,365,343 A | * | 12/1982 | Grady et al. | ................. | 378/181 |
| 4,602,378 A | | 7/1986 | Kelman et al. | ................ | 378/26 |
| 4,736,396 A | * | 4/1988 | Boyd et al. | ...................... | 378/4 |
| 4,741,015 A | * | 4/1988 | Charrier | ...................... | 378/196 |
| 4,922,512 A | | 5/1990 | Lajus et al. | .................. | 378/197 |
| 5,014,293 A | * | 5/1991 | Boyd et al. | ................... | 378/197 |
| 5,247,555 A | * | 9/1993 | Moore et al. | .................. | 378/4 |
| 5,598,453 A | | 1/1997 | Baba et al. | ................... | 378/146 |
| 5,636,259 A | * | 6/1997 | Khutoryansky et al. | .... | 378/197 |
| 5,661,772 A | * | 8/1997 | Bär et al. | ....................... | 378/20 |
| 5,748,696 A | * | 5/1998 | Fujita et al. | .................... | 378/4 |
| 5,841,830 A | * | 11/1998 | Barni et al. | ................... | 378/15 |
| 5,848,126 A | * | 12/1998 | Fujita et al. | ................. | 378/195 |
| 5,949,848 A | * | 9/1999 | Gilblom | ..................... | 378/98.8 |
| 5,960,054 A | * | 9/1999 | Freeman et al. | ................ | 378/4 |
| 6,031,888 A | * | 2/2000 | Ivan et al. | ..................... | 378/20 |
| 6,041,097 A | * | 3/2000 | Roos et al. | .................... | 378/62 |
| 6,113,264 A | * | 9/2000 | Watanabe | .................... | 378/197 |
| 6,149,592 A | * | 11/2000 | Yanof et al. | ................. | 600/427 |
| 6,180,943 B1 | * | 1/2001 | Lange | .................... | 250/363.05 |
| 6,196,715 B1 | * | 3/2001 | Nambu et al. | .............. | 378/197 |
| 6,309,102 B1 | * | 10/2001 | Stenfors | ...................... | 378/197 |

FOREIGN PATENT DOCUMENTS

| | | |
|---|---|---|
| EP | 0 345 138 A1 | 5/1989 |
| GB | 2 167 266 A | 5/1986 |
| WO | WO 92/07512 | 5/1992 |
| WO | WO 94/10908 | 5/1994 |

* cited by examiner

*Primary Examiner*—David V. Bruce
*Assistant Examiner*—Hoon Song
(74) *Attorney, Agent, or Firm*—Carl B. Horton, Esq.; Armstrong Teasdale LLP

(57) ABSTRACT

The present invention, in one form, is a multimode imaging system which, in one embodiment, includes a substantially C-shaped arm movably coupled to a movable base to reduce difficulty of scanning an object. A source assembly having a x-ray source and a detector assembly having a detector are movably coupled to the arm. The source assembly and the detector assembly are independently movable relative to each other and to the arm. In one embodiment, an operator selects one or more modes of operation of the imaging system so that various types of image data are displayed.

16 Claims, 9 Drawing Sheets

MULTIMODE IMAGING SYSTEM FOR GENERATING HIGH QUALITY IMAGES

CROSS REFERENCE TO RELATED APPLICATIONS

This application claims the benefit of U.S. Provisional Application No. 60/114,479, filed Dec. 31, 1998.

BACKGROUND OF THE INVENTION

This invention relates generally to imaging and, more particularly, to scalable multislice imaging systems.

In at least some imaging systems generally referred as computed tomography (CT) systems, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. Total scan time may be further reduced by increasing the number of detector cells in the axis along the patient. An area detector can also be used to collect a volume of data in each rotation.

In a x-ray fluoro system, a flat panel detector can be used to take sequential exposures to track dynamic motion in a patient. This can yield images with high temporal resolution. The images, however, have significant super position artifacts.

In CT fluoroscopic systems ("CT Fluoro"), data collected from a scan may be utilized to generate sequential frames of images. A frame, like a view, corresponds to a two dimensional slice taken through the imaged object. There are no super position artifacts. Particularly, projection data is processed at a frame rate to construct multiple images. With known CT Fluoro systems, the gantry of the CT system is rotated about the area of interest of the patient and sequential images are reconstructed and displayed.

At least one known imaging system utilizes a closed gantry to generate a 3D image of the patient. The 3D images provide object information including depth information. As a result of the closed gantry construction of the CT system, the object is translated through the gantry to generate a 3D image of the object. The translation of the object through the gantry, in addition to being nearly impossible for certain types of objects, causes CT system positioning and use to be difficult.

It would be desirable to provide an multimode imaging system which generates various types of images for the object so that the tradeoffs between devices may be minimized. It also would be desirable to provide such a multimode imaging system which facilitates an open gantry to easy and fast access to the object to be imaged.

BRIEF SUMMARY OF THE INVENTION

These and other objects may be attained by a multimode imaging system which, in one embodiment, includes a substantially C-shaped arm movably coupled to a movable base to reduce difficulty of scanning an object. More specifically, the arm is rotatable and movable relative to the base. A source assembly having a x-ray source and a detector assembly having a detector are movably coupled to the arm. The source assembly and the detector assembly can be independently movable relative to each other and to the arm to adjust image geometry.

In an exemplary embodiment, an operator selects one or more modes of operation of the imaging system. By enabling the system operator to make such selections, different types of image data can be displayed without moving the object or the system. More specifically, and in an exemplary embodiment, the system may be placed relative to the object to be scanned and placed in the selected mode of operation. The movement of the arm and the source and detector assemblies are based upon the mode selected by the operator. Using data collected from the detector, images are generated for the desired area of the object. Images generated in one mode may combined or utilized with images generated in another mode to generate additional images. In another embodiment, the imaging system source and detector may be movably coupled to a large bore rotating gantry.

Additionally, the configuration and the orientation of the detector may be changed to generate additional types of image data. In an exemplary embodiment, the detector includes two detector panels which are angularly positioned relative to each another. Using known references and data collected from the detector panels, specific elements of interest may be located on a 3D image of the object.

The above described multimode imaging system generates various types of images for the object. Such system also enables easy and fast access to the object to be imaged. Such system may be accomplished using a C-arm configuration or with a large bore gantry.

DETAILED DESCRIPTION OF THE INVENTION

Figure 1:
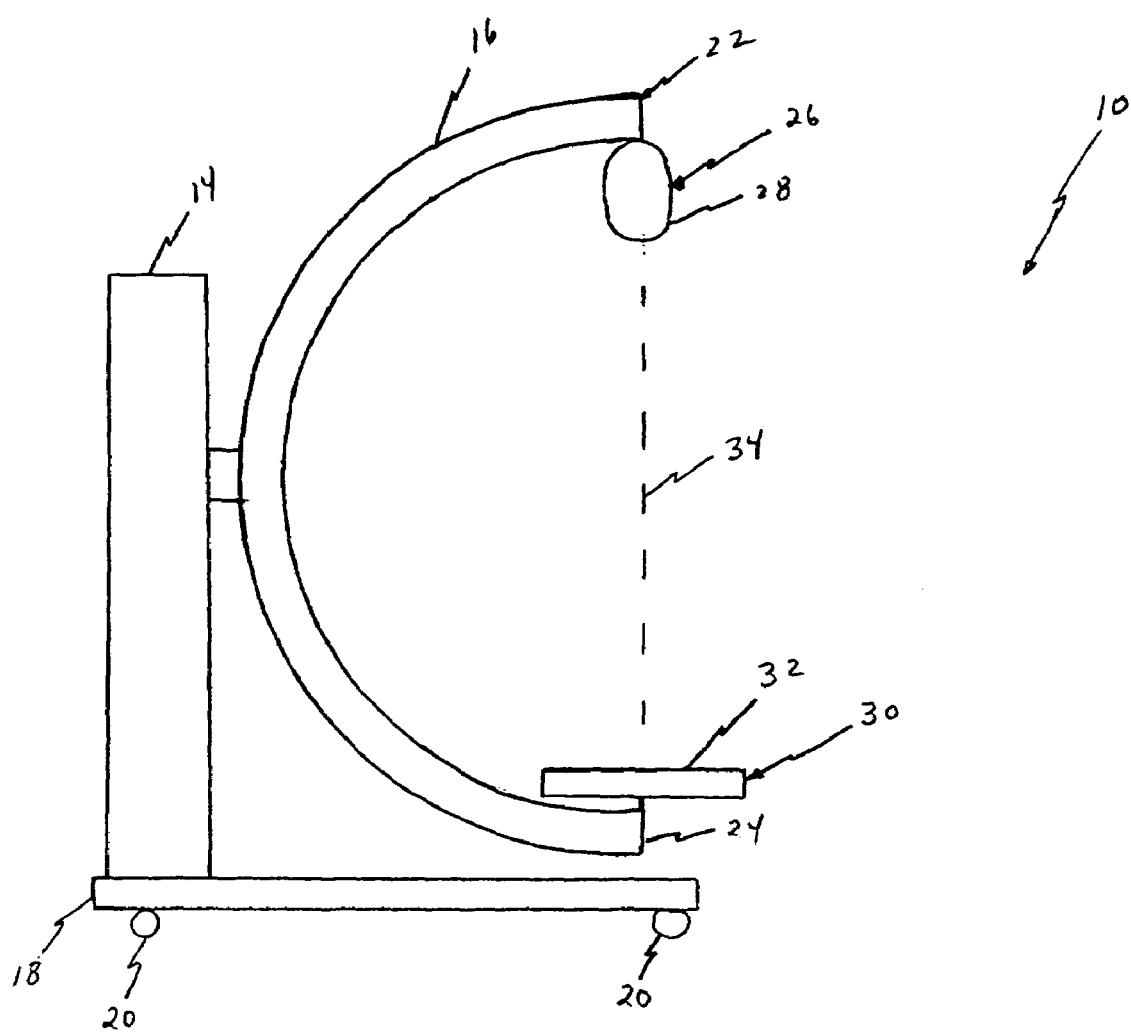
FIG. 1 is a pictorial side view of an imaging system.
Figure 2:
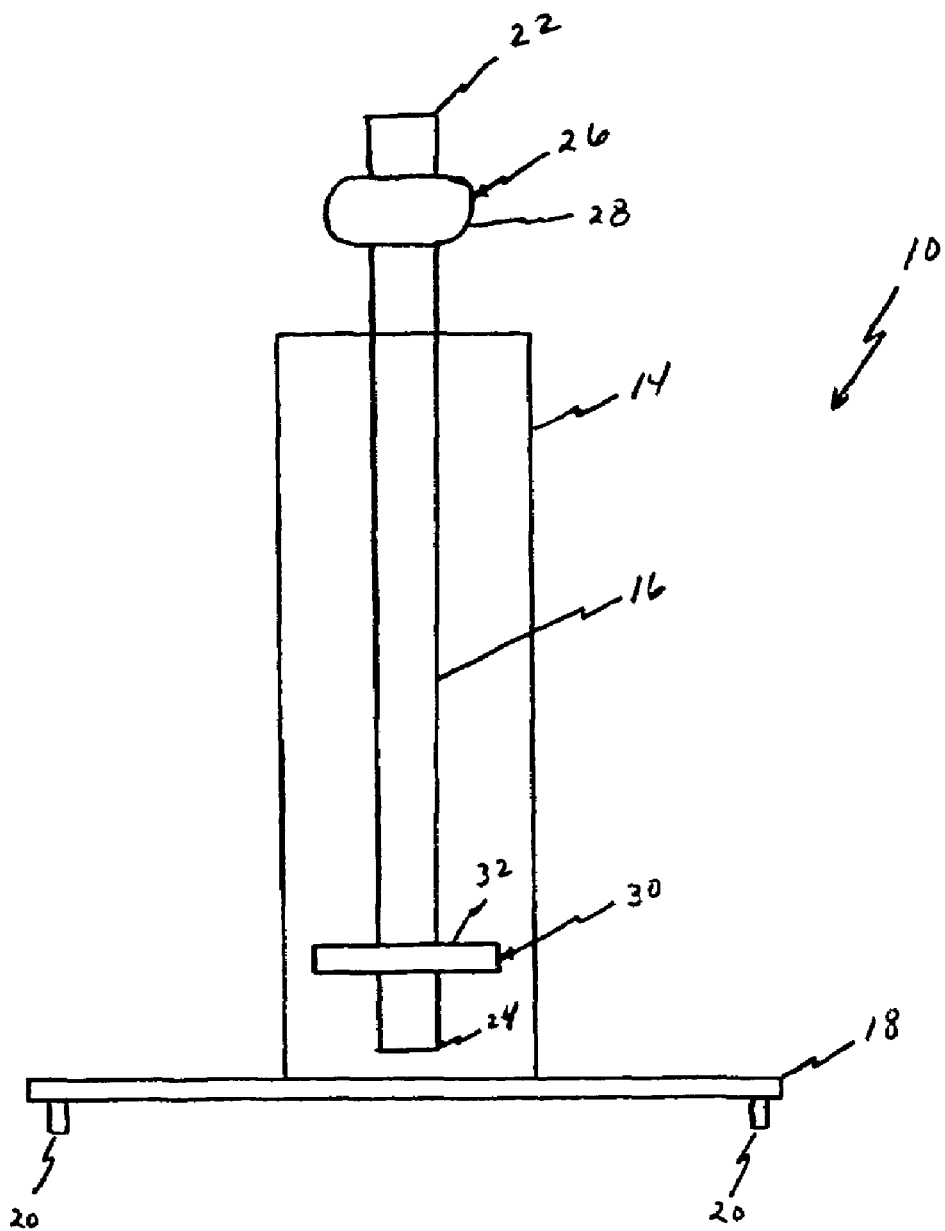
FIG. 2 is a pictorial front view of the system illustrated in FIG. 1.

Referring to FIGS. 1 and 2 and in one embodiment, a multimode imaging system 10 is shown as including a base 14 and a positioning means 16. In one embodiment, base 14 extends from a portable platform 18 having a plurality of wheels 20, or other similar position altering devices, so that system 10 is movable relative to an object to be imaged (not shown in FIGS. 1 and 2). In an alternative embodiment, base 14 is movably coupled and extends from a fixed surface, i.e., a wall (not shown). In one embodiment positioning means 16 includes an arm which is movably coupled to base 14 and includes a first end portion 22 and a second end portion 24. More specifically, arm 16 rotates relative to base 14 about an axis of rotation and moves relative to base 14 to alter the respective distances between arm first end portion 22 and base 14 and arm second end portion 24 and base 14. An x-ray source assembly 26 is movably coupled to arm first end portion 22. X-ray source assembly 26 includes an X-ray source 28 which is configured to emit x-ray signals. A detector assembly 30 is movably coupled to arm second end portion 24. Detector assembly 30 includes a detector 32 and is configured to receive the x-ray signals from said source 28 to generate an image of the object. By moving arm 16 relative to base 14, the position of source assembly 26 may be altered so that source assembly 26 is moved toward or away from base 14. Altering the position of source assembly 26, alters the position of detector assembly 30 relative to base 14 in an opposite direction.

Figure 3:
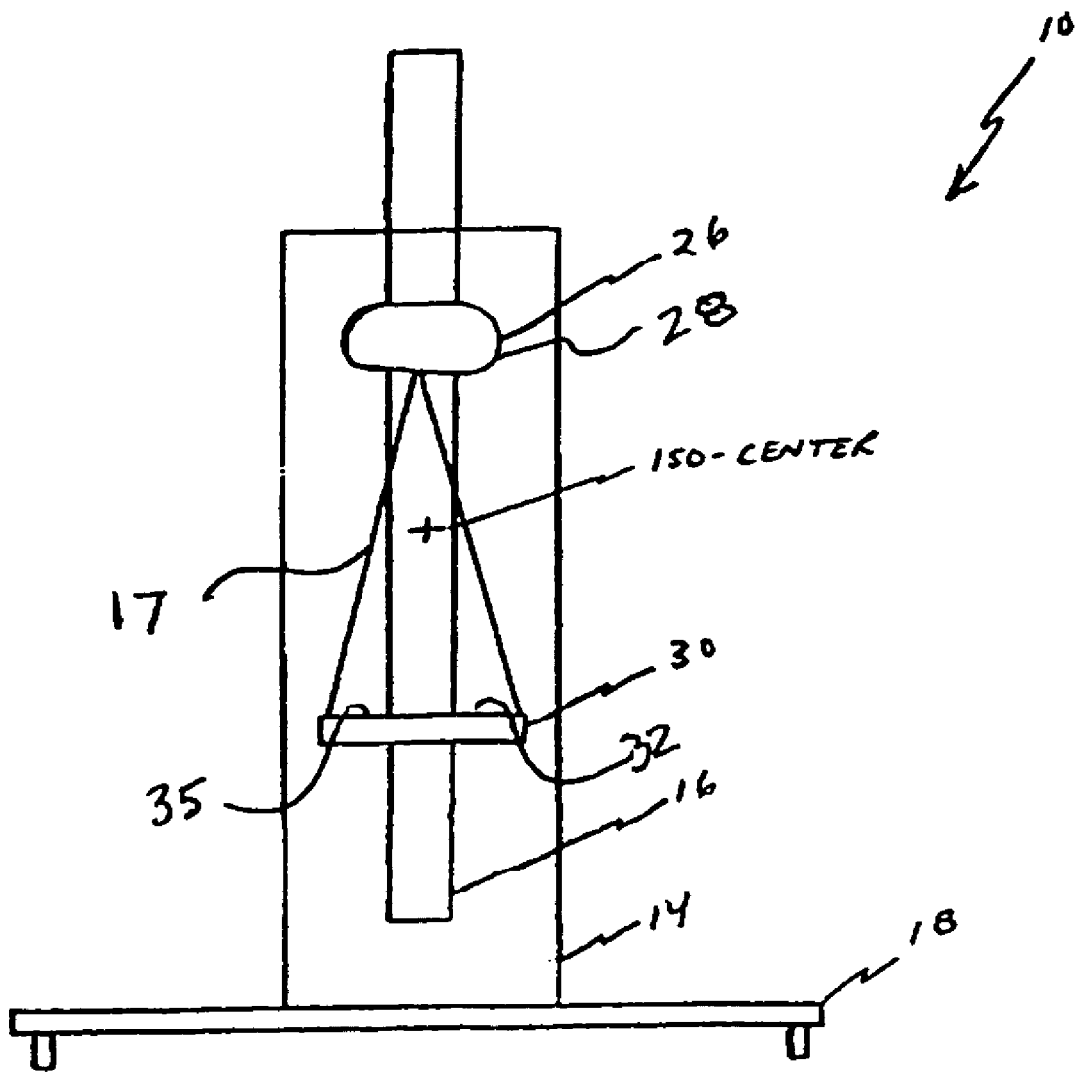
FIG. 3 is a pictorial view of the system illustrated in FIG. 1 representing an altered position of a source and a detector.

More specifically, source 28 and detector 32 are aligned along a plane of interest 34 with respect to the object. Source assembly 26 and detector assembly 30 each independently move relative to each other to alter plane of interest 34 with respect to the object. Additionally, source assembly 26 and detector assembly 30 are each configured to move independent of each other relative to arm 16 to alter a distance between source 28 and detector 32 so that the geometry of system 10 may be varied. More specifically, the position of source assembly 26 and detector assembly 30 may be varied, or altered, so that the respective distances between a system iso-center and source 28 and detector 32 are altered. As shown in FIG. 3, by altering the distance between source 28 and detector 32 and the respective distances to the iso-center of system 10, the magnification factor of system 10 may be modified. The modifiable magnification may be utilized for special imaging needs.

Detector 32, in one embodiment, is formed by a plurality of detector elements 35 which together sense the projected x-rays that pass through the object to collect image data. Detector 32 may be fabricated in a single slice, a multi-slice, or flat panel configuration.

In one embodiment, detector 32 is a solid state detector or radiation imager comprising a large flat panel imaging device having a plurality of pixels 35 arranged in rows and columns. Each pixel 35 includes a photosensor (not shown), such as a photodiode, that is coupled via a switching transistor (not shown) to two separate address lines, a scan line and a data line. In each row of pixels, each respective switching transistor (typically a thin film field effect transistor (FET)) is coupled to a common scan line through that transistor's gate electrode. In each column of pixels, the readout electrode of the transistor (e.g., the source electrode of the FET) is coupled to a data line, which in turn is selectively coupled to a readout amplifier. During nominal operation, x-ray beams 17 passing through the object, for example a patient, being examined are incident on imaging array 32. The radiation is incident on a scintillator material and the pixel photosensors measure (by way of change in the charge across the diode) the amount of light generated by x-ray interaction with the scintillator. As a result, each detector element, or pixel, 35 produces an electrical signal that represents the intensity of an impinging x-ray beam and hence the attenuation of beam 17 as it passes through the object. During a scan to acquire x-ray projection data in one mode defined as a CT volume rotation mode, detector assembly 30 and source assembly 26 are rotated about the object.

In another embodiment of detector 32, x-rays 17 can directly generate electron-hole pairs in the photosensor (commonly called "direct detection"). The photosensor charge data are read out by sequentially enabling rows of pixels (by applying a signal to the scan line causing the switching transistors coupled to that scan line to become conductive), and reading the signal from the respective pixels thus enabled via respective data lines (the photodiode charge signal being coupled to the data line through the conductive switching transistor and associated readout electrode coupled to a data line). In this way a given pixel can be addressed though a combination of enabling a scan line coupled to the pixel and reading out at the data line coupled to the pixel.

Figure 4:
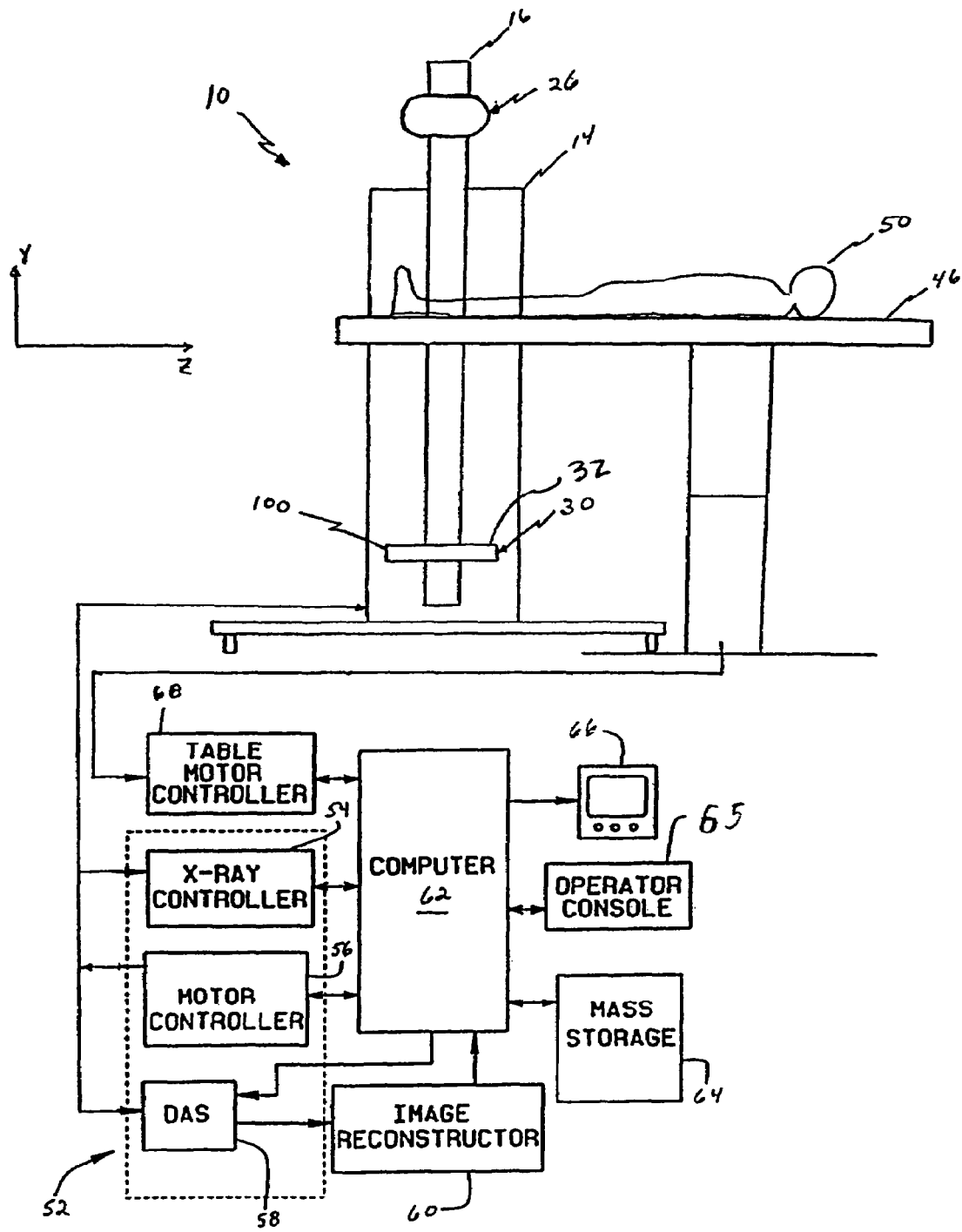
FIG. 4 is a pictorial side view of the system shown in FIG. 1 utilizing a table to support an object.

For example, as shown in FIG. 4, system 10 includes a table 46 for supporting an object 50, i.e., surgical table for supporting a patient. In one embodiment, where base 14 is movable relative to table 46, system 10 may be positioned along either side or end of table 46. To generate an image of patient 50, arm 16 is rotated so that source assembly 26 and detector assembly 30 rotate about patient 50. More specifically, arm 16 is rotatably coupled to base 14 so that detector 32 and source 28 are rotated about object 50. In one embodiment, images are generated by partially rotating arm 16 around patient 50, i.e., arm 16 is rotated 180 degrees plus a fan angle, i.e., approximately 40 degrees, of source 28 around object 50.

In one embodiment, movement of arm 16 and the operation of x-ray source assembly 26 and detector assembly 30 are governed by a control mechanism 52 of system 10. Controller, or control mechanism, 52 includes an x-ray controller 54 that provides power and timing signals to x-ray source 28 and a motor controller 56 that controls the position of arm 16, source assembly 26 and detector assembly 30. A data acquisition system (DAS) 58 in control mechanism 52 samples data from detector 32 for subsequent processing. An image reconstructor 60 receives sampled x-ray data from DAS 58 and performs high speed image reconstruction. The reconstructed image is applied as an input to a computer 62 which stores the image in a mass storage device 64.

Computer 62 also receives commands and scanning parameters from an operator via a console 65 that has a keyboard. An associated cathode ray tube display 66 allows the operator to observe the reconstructed image and other data from computer 62. The operator supplied commands and parameters are used by computer 62 to provide control signals and information to DAS 58, x-ray controller 54 and motor controller 56. Computer 62 operates a table motor controller 68 which controls position of motorized table 46 relative to system 10.

In one embodiment as shown in FIG. 4, detector 32 includes at least one detector panel 100 which is rotatable relative to arm 16. Panel 100 is sized to collect data for an entire organ, section, or region, of object 50, i.e., 40 cm by 40 cm. The area of object 50 to be imaged may be changed by altering, or rotating, detector 32, specifically, panel 100. More specifically, where the shape of panel 100 is non-symmetrical, i.e., having a non-square shape, the orientation of panel 100 may changed to select between a greater coverage area and a greater field of View (FOV). Particularly, panel 100 may be rotated to select the appropriate coverage area and FOV. In addition and again referring to FIG. 3, the area of object 50 to be imaged may be modified by altering the position of detector assembly 30 and/or source assembly 26 so that the distance between source 28 and detector 32 is modified or altered. More specifically, source assembly 26 and detector assembly 30 may be positioned so that only a portion of detector panel 100 is exposed to the x-ray signals emitted from source 28.

In one embodiment, a partially defective panel 100, i.e., known portions of panel elements 35 are non-responsive to x-ray signals, may be utilized to generate images of object 50. This may be accomplished by altering the distance between source 28 and detector 32. Specifically, the distance between source 28 and detector panel 100 is reduced so that the area of x-ray signal exposure is limited to the functioning portion of panel 100. For example, where any number of detector panel elements 35 are non-responsive so that the right 25% of panel 100 is unusable, the distance between detector 32, specifically panel 100, relative to source 28 may be altered so that the data is collected from the remaining 75% of panel 100. In another embodiment, detector panel 100 and/or source 28 may be positioned so that only the center 50% of panel 100 is utilized and the known defective 25% right and a corresponding 25% of the left side of panel 100 are unused to generate the image. The partially defective panel 100 may also be used by collimating x-ray beam 17 from source 28, using a collimator (not shown), so that the defective portion of panel 100 is not exposed to x-rays 17. As a result, x-ray dose to patient 50 is reduced.

Figure 5:
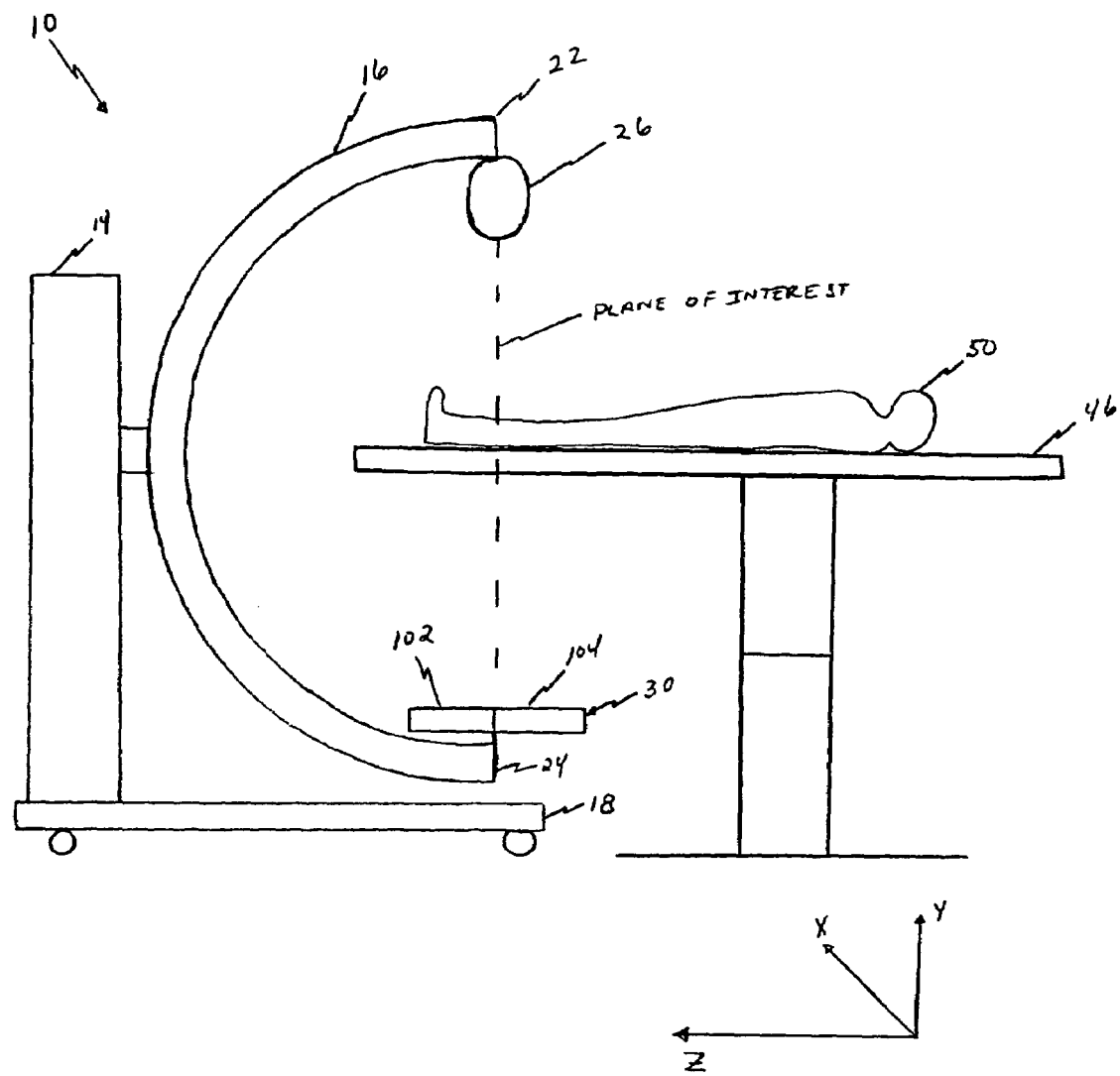
FIG. 5 is a pictorial side view of an alternative position of the system illustrated in FIG. 4 and an alternative embodiment of the detector.
Figure 6:
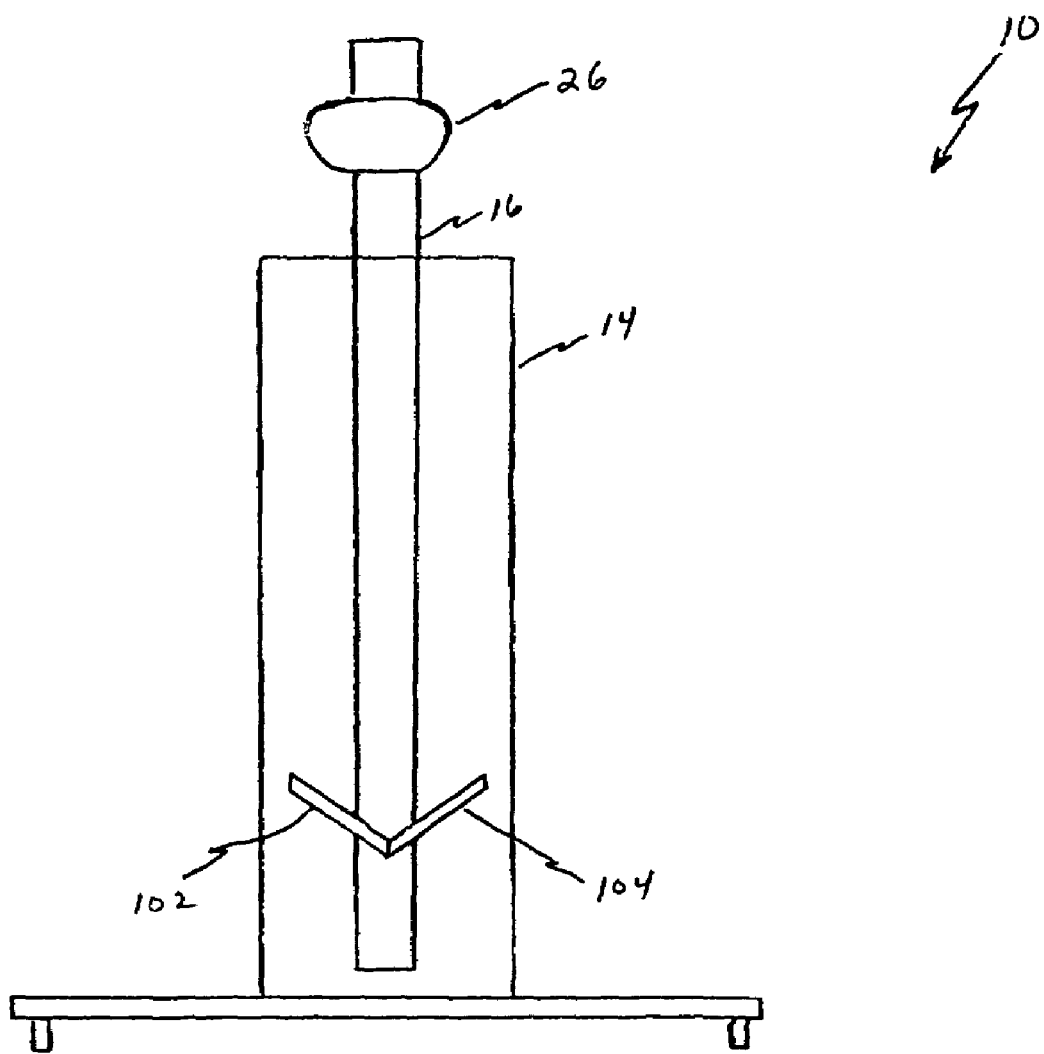
FIG. 6 is a front view of another embodiment of the detector illustrated in FIG. 5.

In another embodiment and referring to FIG. 5, detector 32 includes a first panel 102 and a second panel 104. Panels 102 and 104, are similar to panel 100 and are rotatable relative to arm 16 to alter the field of coverage and the FOV. In one embodiment, panel 102 is positioned adjacent to second panel 104 so that the area of detector 32 includes a combined surface area of panel 102 and panel 104. In another embodiment as shown in FIG. 6, panels 102 and 104 are angularly positioned relative to one another. More specifically and in one embodiment, respective panels 102 and 104 are positioned relative to each other so that the surface of panel 102 is at an obtuse angle with reference to the surface of panel 104. In other embodiments, the angle between respective panels 102 and 104 may range from approximately 0 degrees to approximately 30 degrees. For example, in one embodiment panel 102 is positioned perpendicular to panel 104.

In operation, system 10 is configured to operate in at least one of a plurality of modes including for example, Computed Tomography (CT) volume axial rotating, CT volume helical rotating, CT volume sliding, X-ray Fluoro, and CT tomosynthesis modes. Initially an operator determines, or selects, a first, or initial, mode of operation for system 10, for example using computer 62. The position and movement of arm 16, source assembly 26 and detector assembly 30 are based on the selected mode of operation of system 10. More specifically, the position and movement of arm 16 relative to base 14 and source assembly 26 and detector assembly 30 relative to each other, arm 16, and the object are altered, or controlled, by the operator selected mode. After collecting data utilizing detector assembly 30, at least one image of object 50 is generated. The operator may then generate additional images using existing mode or may select one of the other modes of system 10. The operation of system 10 for the CT volume rotating, CT volume sliding, CT fluoro, and CT tomosynthesis modes are described below in further detail below.

CT Volume Rotating

Prior to selecting the CT volume rotating mode of system 10 by the operator, system 10 is positioned relative to object 50. As a result of the shape of arm 16, system 10 may be easily positioned adjacent to table 46. For example and referring again to FIG. 5, where images are desired of a certain area of object 50, i.e., the lower portion of a patient's leg, system 10 is placed relative to table 46 so that arm 16 rotates about table 46. More specifically, system 10 is positioned near the end of table 46 so that as arm 16 rotates about a axis of object 50, source assembly 26 and detector assembly 30 move relative to table 46. Particularly and in one embodiment, arm 16 rotates about 180 degrees plus a fan angle about base 14. Arm 16 is rotated relative to base 14, source assembly 26 and detector assembly 30 are rotated about object 50 and table 46. X-rays signals are emitted from source 28 and collected by detector 32 as arm 16 is rotated. The signals collected from detector 32 are processed in a manner known in the art to generate an image of object 50, i.e., an image along the plane of interest of the patient's leg. More specifically and in one embodiment, arm 16 rotates about base 14 at a fairly slow speed, i.e., 3 to 10 seconds per rotation, and data is collected for each row of elements 32. Reconstructed images are then generated using data collected from elements 35 of detector 32. In one embodiment, the reconstructed images for each row of detector 32 are then combined to form a 3D image of object 50. The 3D image, in one embodiment, is a volume display, to understand the location of the elements contained within object 50, for example the bones within the patient. As described above, where detector 32 is non-symmetrical, the orientation of detector 32 may be altered to select the appropriate coverage area, i.e., a larger X-axis coverage area, and Field of View (FOV), i.e., a larger Z-axis coverage area. After the images are generated, the operator may reposition system 10 relative to object 50 or select a different mode of operation. In addition, if the operator has completed all tasks, system 10 may be removed without interfering with or disturbing object 50.

CT Volume Sliding

Figure 7:
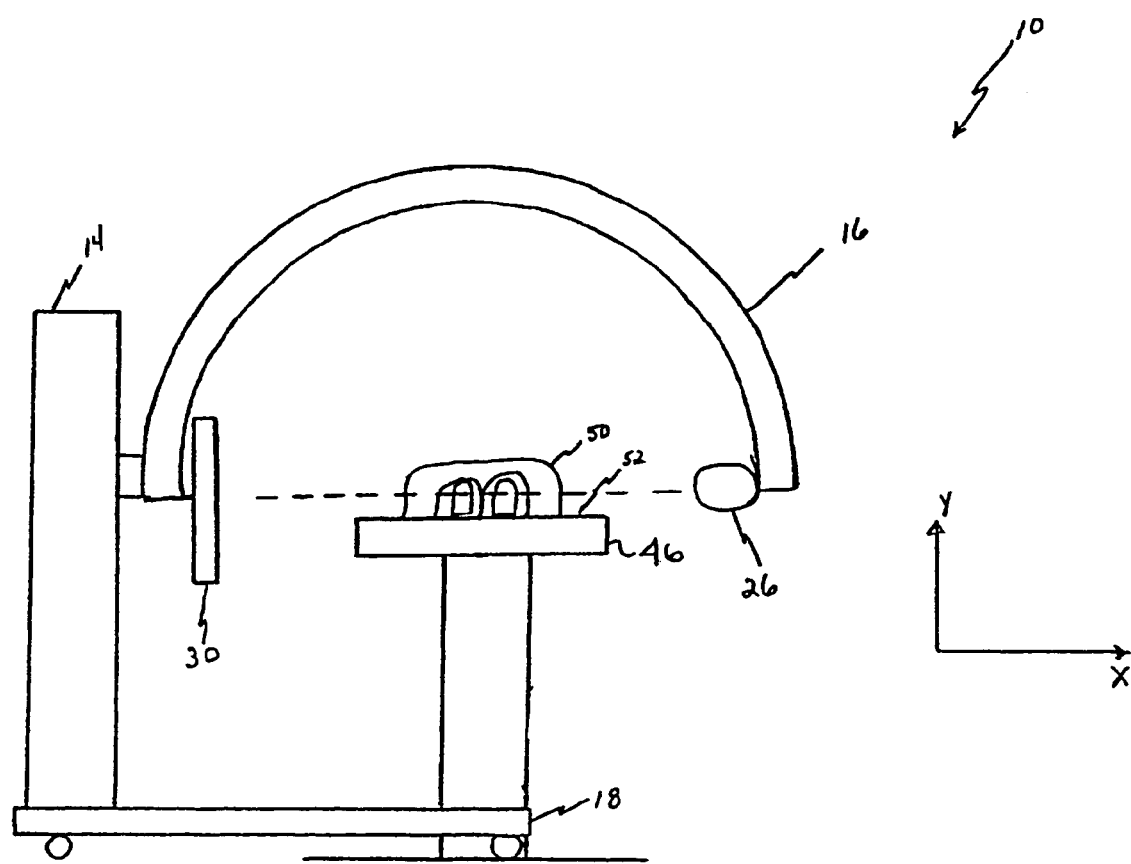
FIG. 7 is pictorial side view of the system illustrated in FIG. 1 in a CT volume sliding mode.

The CT volume sliding mode allows image generation of objects having a shape, placement, or configuration which are difficult or impossible to image using known imaging systems. More specifically, and as shown in FIGS. 4 and 7 where system 10 is placed along one of the sides of table 46, arm 16 is moved relative to base 14 so that source assembly 26 and detector assembly 30 are moved perpendicular to table 46. Particularly, as arm 16 is moved relative to base 14, source assembly 26 and detector assembly 30 traverse around object 50 so that plane of interest 34 is parallel to surface 52 of table 46. For example as shown in FIG. 7, in order to scan object 50 positioned on table 46, arm 16 is moved relative to base 14 so that the respective distances between arm first end portion 22 and base 14 and between second end portion 24 and base 14 are altered. More specifically and in one embodiment, arm 16 is moved relative to base 14 so that source assembly 26 is a maximum distance from base 14 and detector assembly is a minimum distance from base 14.

To generate an image of object 50, source 28 is enabled to emit x-ray signals toward detector 32 and arm 16 is moved relative to base 14 so that source assembly 26 is moved closer to base 14. In one embodiment, arm 16 is moved relative to base 14 so that source assembly 26 and detector assembly 30 scan 180 degrees plus a fan angle of source 28 traverse to object 50. 3D images are then generated in a similar manner as described above in the CT volume rotating mode. After the images are generated, the operator may reposition system 10 relative to object 50 or select a different mode of operation. In addition, if the operator has completed all tasks, system 10 may be removed without interfering with or disturbing object 50.

X-ray Fluoro Mode

Figure 8:
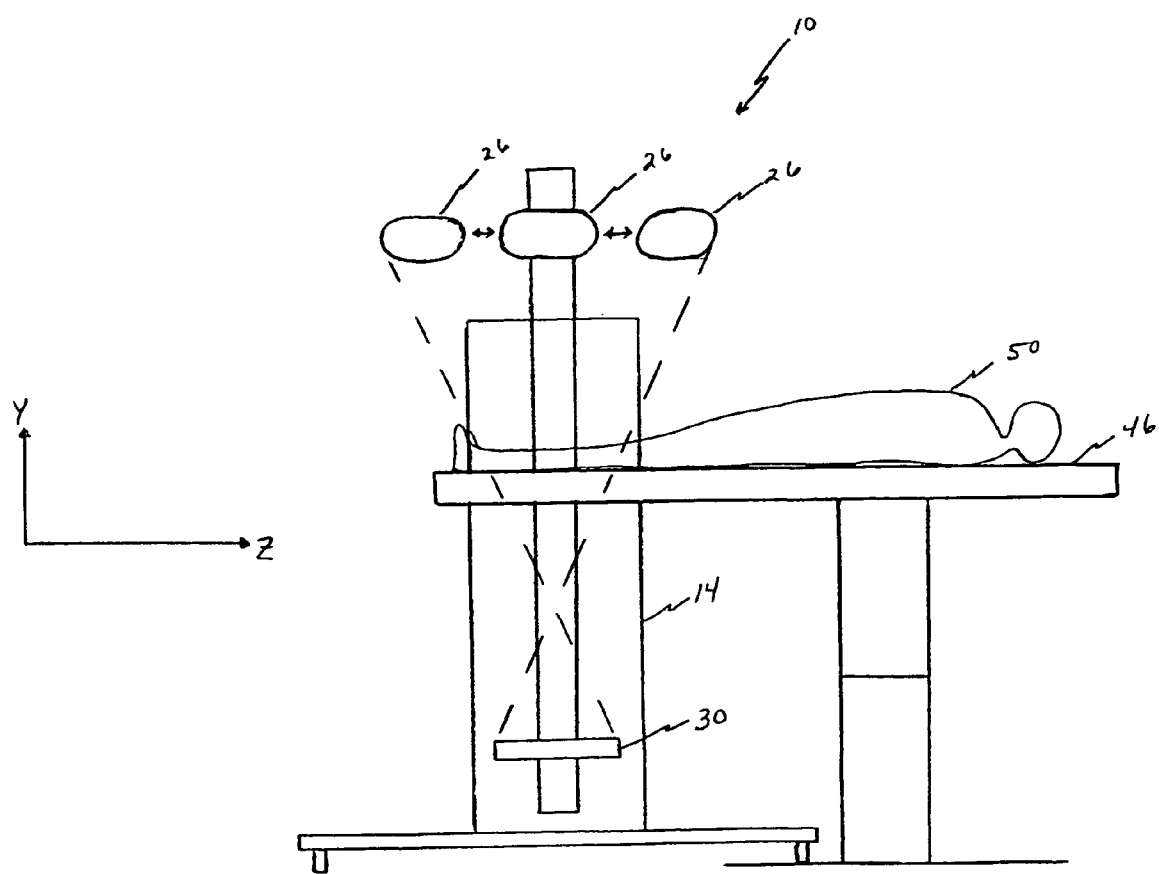
FIG. 8 is pictorial side view of the system illustrated in FIG. 1 in a x-ray fluoro mode.

Once at least one 3D image has been generated for object 50 using one of the other modes, system 10 is placed into the X-ray fluoro mode to locate in elements within object 50. In one embodiment as shown in FIG. 8, where system 10 is positioned along one side of table 46, arm 16 is positioned relative to object 50 and is fixed in position, i.e., arm 16 is positioned so that plane of interest 34 is parallel to base 14 and source assembly 26 and detector assembly 30 are an equidistance from base 14. The distance between source 26 and detector 30 is then adjusted for the selected area to be scanned. Source 28 is then enabled and image data is collected. Source 28 can then be translated along the axis of object 50, i.e., the patient, to locate the desired element within the object, i.e., a bone of interest, as the position of detector 32 remains fixed. As source 28 is translated, a series of real-time images along plane of interest 34 are generated in accordance with known fluoroscopy methods to determine the location of the desired element within object 50. A pseudo three dimensional image may then be generated by combining multiple images taken at different angles. This will yield additional depth information not found in a conventional single position image.

In another embodiment, source 28 is angularly translated relative to object 50 to determine the location of the bones of interest in the 3D image. More specifically, source 28 is shifted, or moved, toward or away from detector assembly 30 in addition to the Z-axis translation so that source 28 is angularly translated relative to object 50 to generate the real-time images.

In another embodiment, the location of the desired elements, i.e., bones of interest, may be directly determined using data collected from detector panels 102 and 104. More specifically and referring to FIG. 6, where respective panels 102 and 104 are angularly positioned relative to one another, separate images are generated for respective panels 102 and 104. After determining the location of known references in the separate images generated from panels 102 and 104, the location of the bones of interest on the 3D image are directly determined utilizing known triangulation methods. More particularly and in one embodiment, utilizing a dual spot source 28 and linear translation of source 28, the location on the 3D images is determined.

For example, after generating the 3D images using one of the CT volume modes, the operator places system 10 in the fluoro mode. Using the generated fluoro mode real-time images, the operator, for example a doctor, may locate at least one bone of interest. In addition, the fluoro images may be utilized to display and determine the location of other devices with respect to the bone of interest. For example, the image may be utilized to locate medical screws to be inserted into the bone of interest. Specifically, the images may be utilized to predict, or determine, the trajectory of a medical instrument, for example, a drill, with respect to the bone of interest. This may also be accomplished by instructing the screw or instrument position device. After the images are generated, the operator may reposition system 10 relative to object 50 or select a different mode of operation. In addition, if the operator has completed all tasks, system 10 may be removed without interfering with or disturbing object 50.

Tomosynthesis Mode

Figure 9:
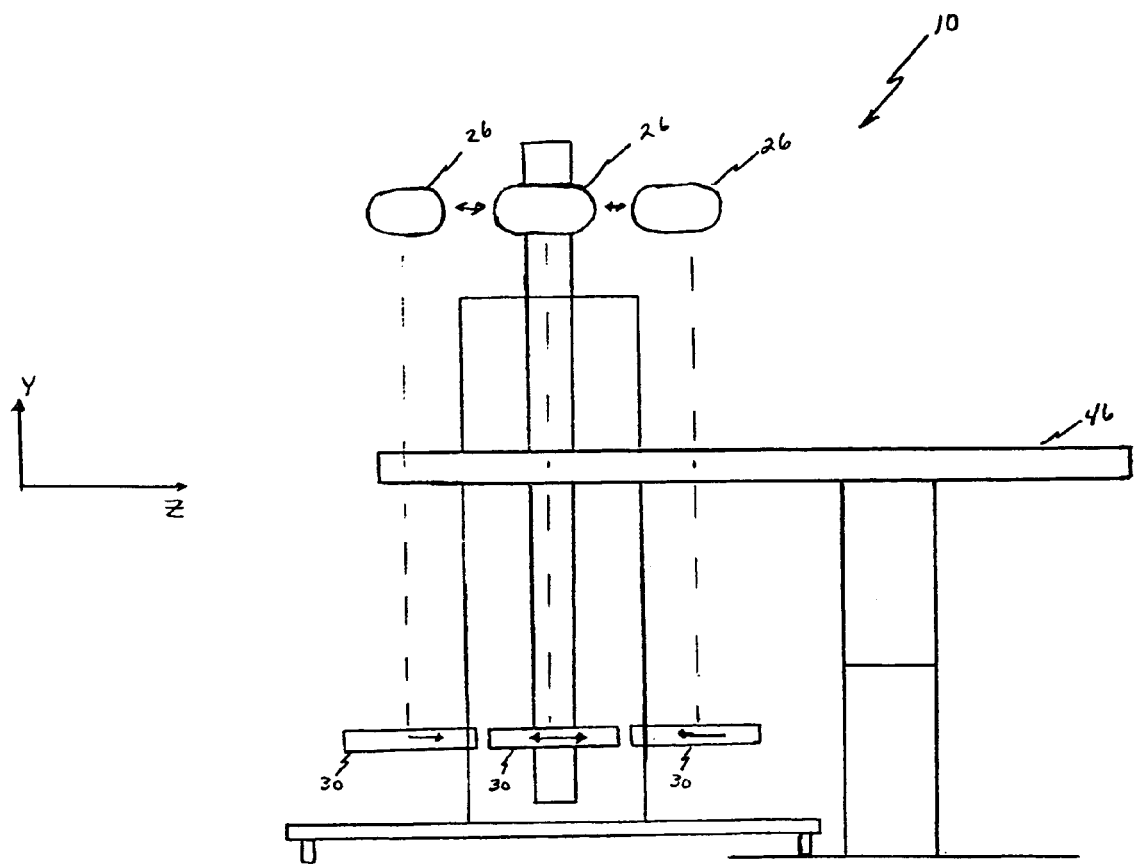
FIG. 9 is pictorial side view of the system illustrated in FIG. 1 in a tomosynthesis mode.

In the tomosynthesis mode, at least one plane of interest image is generated using system 10. Specifically and referring to FIG. 9, each plane of interest image includes a single plane of the object which is in focus and all remaining information contained in the image is blurred. More specifically and in one embodiment, source assembly 26 and detector assembly 30 are positioned so that plane of interest 34 is aligned with the desired object image plane of interest. In another embodiment, a series of plane of interest images are generated by translating source assembly 26 and detector assembly 30 together parallel to the desired object plane of interest. For example, where system 10 is placed along one side of table 46 and plane of interest 34 is perpendicular to table 46, source assembly 26 and detector assembly 30 are translated together along the axis of object 50 to generate an image of each desired plane of interest 34. In another embodiment, source 28 may be angularly translated as described above, as detector assembly 30 is translated to generate the series of images. In one embodiment, the series of plane of interest images are then digitally combined to generate a stack of images representative of the image volume.

Use

In use, system 10 may be utilized to generate different types of images and information for object 50. For example in medical applications, a patient 50 lying on table 46, i.e., an emergency room table or a surgical table, may be scanned. As a result of the portability of system 10 and the shape of arm 16, system 10 may be quickly positioned relative to patient 50 without interfering with the numerous devices which are typically coupled to patient 50. In addition, system 10 may be positioned in a plurality of positions to scan the desired area of patient 50 without moving patient 50. Additionally, the mode of system 10 may be altered to generate different types of images to provide further assistance in providing aid to patient 50. More specifically and in one embodiment, an operator selects at least one mode of operation for system 10 utilizing the keyboard. Computer 62 supplies the appropriate signals to control mechanism 52 control the movement of positioning means 16, source assembly 26, and detector assembly 30. In addition, where the operator desires to generate an image utilizing more than one mode, the operator may select at least additional mode using computer 62. More specifically, the operator may configure system 10 so that at least one image from a first mode of operation may be combined with at least one image from at least a second mode of operation. As a result of the combination of the images, image quality is improved.

In industrial applications, system 10 may be utilized to generate images for objects which are typically difficult or impossible to scan. For example, a piece of equipment that is fixed in position and coupled to other equipment may be scanned using system 10. Specifically, as a result of the shape of arm 16, source 28 and detector 32 may be utilized to generate images of the object.

In another embodiment of system 10, positioning means 16 is a large bore gantry (not shown). Gantry 16 is rotatably coupled to base 14 and source assembly 26 and detector assembly 30 are movably coupled to gantry 16. In one embodiment, gantry 16 includes a large bore (not shown) of approximately 80 to over 100 cm in diameter. The large bore provides adequate clearance to scan a patient 50 positioned on a large surgical table (not shown). In addition to altering the position of source assembly 26 and detector assembly 30 as described above, gantry 16 rotates source assembly 26 and detector assembly 30 around patient 50.

The above described multimode imaging system generates various types of images for the object. Such system also enables easy and fast access to the object to be imaged. Such system may be accomplished using a C-arm configuration or with a large bore gantry.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. An imaging system for generating an image of an object, said imaging system comprising a base, a mechanical positioning means movably attached to said base, an x-ray source assembly comprising an x-ray source configured to emit x-ray signals and attached to said mechanical positioning means, and a detector assembly comprising a detector attached to said mechanical positioning means, said system configured to:
   enable an operator to select a mode of operation from a plurality of modes of the imaging system, said plurality of modes including a computed tomography mode in which said mechanical positioning means rotates through an angle of 180 degrees plus a fan angle, said x-ray source emits x-rays and said detector assembly collects signals, and in which an image in said computed tomography mode is generated utilizing said collected signals;
   alter the position of said detector assembly and said source assembly relative to said other assembly and the object based on the selected mode; and
   generate an image of the object, and wherein to generate an image of the object, said system is configured to radiate x-ray signals from said x-ray source toward said detector assembly, wherein said detector assembly comprises a first detector panel and a second detector panel, and wherein to collect image data, said system is configured to angularly position said first detector panel relative to said second detector panel at least one of acutely or perpendicularly; and
   said system further configured to enable the operator to select at least one additional mode of operator from the plurality of modes of the imaging system for imaging the object.

2. A system in accordance with claim 1 wherein to enable the operator to select a mode, said system is configured enable the operator to select at least one of an x-ray fluoro mode and a tomosynthesis mode.

3. A system in accordance with claim 1 wherein to alter the position of said detector assembly and said source assembly, said system is configured to rotate said positioning means relative to said base so that said detector assembly and said source assembly are rotated about the object.

4. A system in accordance with claim 1 wherein to alter the position of said detector assembly and said source assembly, said system is configured to move at least one of said source and said detector relative to said other assembly to alter a distance between said source and said detector.

5. A system in accordance with claim 1 wherein said source and said detector are aligned along a plane of interest, and wherein to alter the position of said detector assembly and said source assembly, said system is configured to move at least one of said source and said detector relative to said other assembly to alter the plane of interest.

6. A system in accordance with claim 5 wherein to move at least one of said source and said detector relative to said other assembly, said system is configured to translate at least one of said source and said detector parallel to the plane of interest.

7. A system in accordance with claim 1 further comprising a table for supporting the object, and wherein to alter the position of said detector assembly and said source assembly, said system is configured to move said detector and said source relative to said table.

8. A system in accordance with claim 7 wherein to move said detector assembly and said source assembly relative to said table, said system is configured to rotate said detector assembly and said source assembly about said table.

9. A system in accordance with claim 1 wherein to collect image data, said system is configured to detect x-ray signals utilizing a portion of at least one said detector panel and to alter a position of at least one of said detector panel.

10. A system in accordance with claim 1 wherein said positioning means comprises an arm having a first end portion and a second end portion, wherein said x-ray source assembly coupled to said arm first end portion, and wherein said detector assembly coupled to said arm second end portion.

11. A system in accordance with claim 1 wherein said positioning means comprises a gantry rotatably coupled to said base.

12. A method of generating an image of an object using a multimode imaging system configured to operate in a plurality of modes of operation, said method comprising the steps of:
   generating an image of the object in a first mode of operation;
   generating an image of the object in a second mode of operation; and
   configuring the multimode imaging system to combine at least one image from the first mode of operation with at least one image from the second mode of operation to thereby improve image quality;

wherein at least one said mode of operation is an x-ray fluoro mode wherein separate images of the object are generated using respective detector panels that are angled with respect to one another and wherein the multimode imaging system is configured to determine a location of desired elements in the separate images.

13. A method in accordance with claim 12 wherein the plurality of modes of operation comprise a plurality of modes selected from the group consisting of computed tomographic modes, X-ray fluoro mode, and tomosynthesis mode.

14. A method in accordance with claim 12 wherein at least one of the modes of operation includes an x-ray fluoro mode and another includes a 3-D image mode, wherein the first mode of operation is the 3-D image mode and the second mode of operation is the x-ray fluoro mode, and the second mode of operation is used to predict or determine the trajectory of a medical instrument with respect to the desired element location.

15. A method of generating an image of an object using a multimode imaging system configured to operate in a plurality of modes of operation, said method comprising operating the imaging system in a 3-D image mode to generate a 3-D image and then operating the imaging system in an x-ray fluoro mode to generate a plurality of images taken at different angles relative to the object, and using the generated plurality of images to locate a desired element in three dimensions in the 3-D image, and further wherein said generating a plurality of images in said x-ray fluoro mode comprises utilizing angled detector panels to generate separate x-ray fluoro images, determining a location of the desired element within the separate x-ray fluoro images, and utilizing triangulation from the determined location of the desired element within the separate x-ray images to determine a location of the desired elements in the 3-D image.

16. A method in accordance with claim 15 wherein the angled detector panels are oriented perpendicularly or at an acute angle to one another.

* * * * *